United States Patent [19]

Bierbaum et al.

[11] Patent Number: 5,007,831
[45] Date of Patent: Apr. 16, 1991

[54] DENTAL HANDPIECE COMPRISING A GRIP PART

[75] Inventors: Thomas Bierbaum, Lorsch; Johann Hain, Heppenheim-Kirschhausen, both of Fed. Rep. of Germany

[73] Assignee: Siemens Aktiengesellschaft, Berlin and Munich, Fed. Rep. of Germany

[21] Appl. No.: 346,734

[22] Filed: May 3, 1989

[30] Foreign Application Priority Data

May 16, 1988 [DE] Fed. Rep. of Germany ....... 3816612

[51] Int. Cl.⁵ ............................................... A61C 3/00
[52] U.S. Cl. .................................................... 433/114
[58] Field of Search ............... 433/133, 132, 114, 116, 433/131; 81/489; 7/167, 168; 74/551.9

[56] References Cited

U.S. PATENT DOCUMENTS

| 577,063 | 2/1897 | Pedersen | 433/114 |
|---|---|---|---|
| 641,006 | 1/1900 | Geddes | 433/114 |
| 1,470,100 | 10/1923 | Porter | 433/114 |
| 3,060,581 | 10/1962 | Aymar et al. | 433/133 |
| 3,093,172 | 6/1963 | Reed II | 81/489 |
| 3,132,426 | 5/1964 | White | 433/132 |
| 3,364,576 | 1/1968 | Kern, Jr. | 433/132 |
| 3,380,162 | 4/1968 | Heathe | 433/132 |

FOREIGN PATENT DOCUMENTS

| 0017861 | 10/1980 | European Pat. Off. |  |
|---|---|---|---|
| 0054653 | 6/1982 | European Pat. Off. |  |
| 682545 | 10/1939 | Fed. Rep. of Germany |  |
| 3002875 | 2/1981 | Fed. Rep. of Germany |  |
| 3142534 | 5/1983 | Fed. Rep. of Germany | 433/114 |

Primary Examiner—Cary E. Stone
Attorney, Agent, or Firm—Hill, Van Santen, Steadman & Simpson

[57] ABSTRACT

In order to provide a surface in a gripping region of a dental handpiece that meets the requirements of being optimally smooth for hygienic reasons and also to provide an adequate non-slip surface, the dental handpiece has a plurality of thin lines arranged in line patterns having a roughened surface in the gripping portion. These lines or line patterns extend in a longitudinal direction and may have portions that extend at an angle to the longitudinal portion, and these patterns are arranged at least in two quadrants of the circumference of the grip part that preferably lie diametrically opposite one another.

15 Claims, 1 Drawing Sheet

DENTAL HANDPIECE COMPRISING A GRIP PART

BACKGROUND OF THE INVENTION

The present invention is directed to a dental handpiece that contains a grip part having a non-slip surface.

Apart from a few exceptions, dental handpieces are usually held in the fashion of a pencil, for example in a three-finger hold or grip. The surface design in the region of the finger hold, which region is referred to as a gripping region, plays a particular part with the quality of the grip.

For hygienic reasons, particularly because of easy cleaning of the surface of the handpiece, first, one aim is that the entire handpiece should comprise an optimally smooth surface. On the other hand, it is necessary to have adequate gripability in the gripping region to enable the handpiece to lie securely in the hand during a preparation without great finger pressure. This is true both with respect to turning as well as with respect to longitudinal slippage under the influence of axial and radial forces that act on the drill during the use of the drill.

In order to meet these contradictory demands, it has already been proposed to provide a plurality of trough-shaped flattened portions or depressions uniformly distributed over the circumference of the handpiece in the gripping region. Such an arrangement is disclosed in European Patent Application EP-A-00 17 861. With the aim of reducing the manufacturing cost for the surface fashioning of the handpiece, it has also been proposed, in European Patent Application EP-A-00 54 653, to provide the surface of the handpiece in the gripping region with a carrier layer in which grains of a defined size are embedded. The handpiece will exhibit a certain roughness and, thus, gripability in the gripping region.

Although good gripability is obtained with this surface design, the problem or, respectively, the question whether such a surface is not too anti-slip is raised to a great extent, particularly in view of the greater and greater demand currently occurring for the wearing of rubber gloves when using a dental handpiece.

SUMMARY OF THE INVENTION

The object of the present invention is to provide a non-slip surface on a dental handpiece which has a surface design for the gripping region that is less involved in terms of production technology, that comes even closer to the demand for optimally smooth surfaces and can be more easily cleaned than do previously embodiments but, on the other hand, nonetheless, exhibits adequate gripability in the aforementioned sense.

To accomplish these goals, the improvement in the grip non-slip surface is that the non-slip surface is formed by a plurality of thin lines having a roughened surface which extends in a longitudinal direction and/or in a transverse or crosswise direction of the handpiece, said lines being arranged in at least two quadrants of the circumference of the dental handpiece and, preferably, the quadrants lie diametrically opposite one another.

The inventively proposed measures allow the portions of rough surface required for the gripability to be considerably reduced without the gripability being thereby deteriorated. Even when the inventively proposed line patterns are placed extremely close to one another, the surface portions of the rough surface would still be considerably less than in a handpiece whose surface in the grip region is fashioned with embedded grains in accordance with the known coating technique mentioned hereinabove. Additional advantages of the inventively proposed measures are that the cost for the surface fashioning is considerably more cost beneficial than the measures previously proposed and that labels for the handpiece can be provided at the same time with this method.

The lines can be closed or interrupted, for example can be formed by being joined to one another in a punctiform fashion. They can also form open or closed line patterns. The lines or, respectively, line patterns are applied to the circumference of the handpiece so that the fingers are always in contact with one or more lines, given the standard three-finger hold or grip, so that the fingers will always encounter narrow zones having a rough surface. The lines or, respectively, the line patterns can proceed either in a longitudinal direction, in a transverse direction or in both directions as well. The combination of longitudinal, transverse proceeding lines or, respectively, line patterns proves especially advantageous in order to be able to offer the handpiece better resistance, given pushing or pulling preparations. It should be pointed out in this context that the term "transverse" is not to be understood in the narrow sense of exactly 90° arrangement relative to the longitudinal proceeding lines or line courses, but is to define lines which either extend across the longitudinally extending lines or forms an angle with the longitudinally extending lines.

The transversely and longitudinally proceeding line patterns can be advantageously self-contained and form geometrical figures or designs. It is advantageous to arrange a plurality of the geometrical figures in close proximity, preferably overlaying or overlapping one another. The line courses can be provided uniformly distributed over the surface of the grip part, and the arrangement of lines or, respectively, line patters or geometrical figures at the surface of the two quadrants of the handpiece that preferably lie diametrically opposite one another is always adequate. The method for applying the lines or, respectively, the line patterns can occur by partially roughening the surface with a laser beam, by sandblasting or by an etching process.

Other advantages and features of the invention will be readily apparent from the following description of the preferred embodiments, the drawings and claims.

DESCRIPTION OF THE PREFERRED EMBODIMENTS

Figure 1:
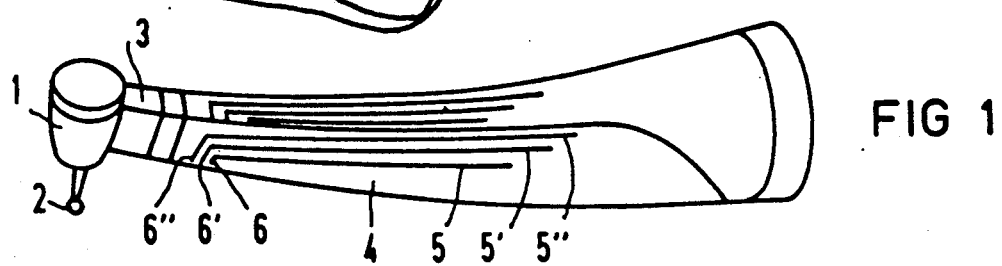
FIG. 1 is a side perspective view of a dental handpiece in accordance with the present invention.

The principles of the present invention are particularly useful when incorporated in a dental handpiece, illustrated in FIG. 1. The dental handpiece of FIG. 1 has a head housing 1, which contains means for rotating a tool 2 on the axis of the tool. The head housing 1 has a neck part 3 which is interconnected to a grip part 4. The grip part 4 contains connections, not shown in greater detail, for supply hoses which are on the right-hand side of the grip part. Since the present invention is directed to the surface of the grip part 4, the contents, which are conventional, of the grip part are not shown or described.

Figure 2:
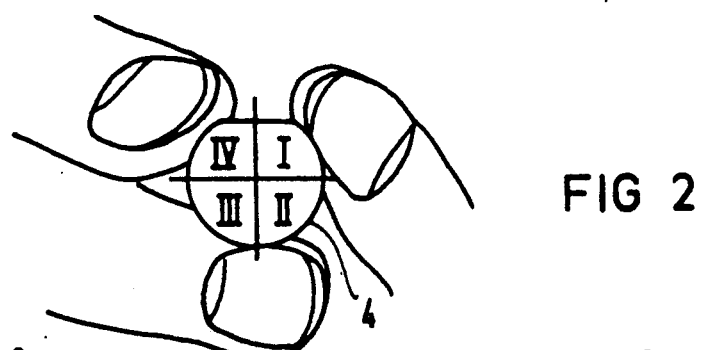
FIG. 2 is a schematic front view of the handpiece in accordance with the present invention illustrating the gripping of the handpiece.

As schematically illustrated in FIG. 2, a handpiece of the illustrated type is held in the fashion of a pencil, for example with the thumb, the index finger and middle finger, gripping the handpiece in a gripping region at three locations around the circumference of the handpiece. When the cross section of the grip part is divided into four quadrants I, II, III, IV, then contact between the fingers surrounding the handpiece is established at the surface of all four quadrants. When the handpiece is held with only two fingers, this potentially, likewise occurs given a specific preparation when the contacting of the handpiece at the circumference of at least two quadrants is established. Under these points of view, the various modifications of the grip-beneficial design of the surface set forth in greater detail hereinbelow can be arranged at the surface of two or more quadrants of the handpiece. If only in two quadrants, preferably they are the two quadrants which are diametrically opposite one another.

Figure 3:
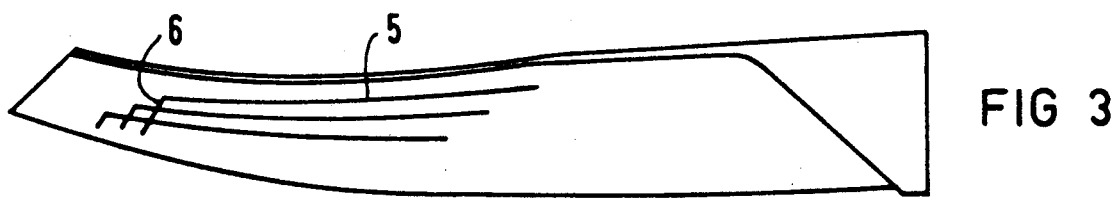
FIG. 3 is a side view of a portion of the handpiece of FIG. 1.

In the exemplary embodiment of FIG. 1, the non-slip surface is formed by a plurality of thin lines, 5, 5', 5'', which are arranged in tight proximity next to one another and which, adjacent the head housing 1, merge into transversely proceeding lines or portions 6, 6' and 6'', respectively. The portions 6, 6' and 6'' extend at an angle to the lines or portions 5, 5' and 5'', respectively. These groups of lines form a plurality of line patterns 5, 6; 5', 6'; and 5'', 6''. These line patterns are arranged in tight proximity next to one another in the embodiment of FIG. 1 but do not touch one another. However, in the modification of FIG. 3, they may cross one another.

Figure 4:
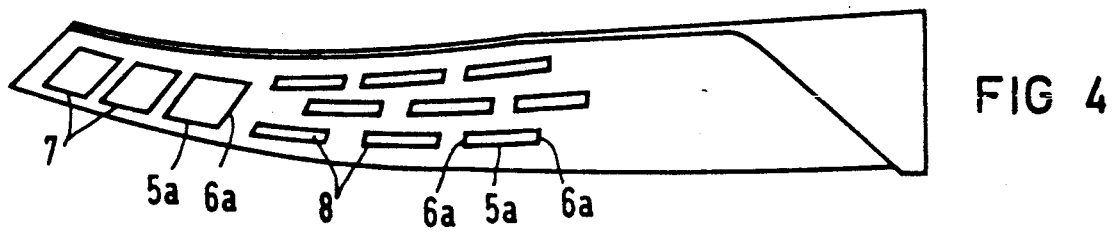
FIG. 4 is a side view of a first modification of a line pattern for the handpiece of FIG. 1.
Figure 5:
FIG. 5 is a side view of a portion of the handpiece of FIG. 1 showing a second modification of the line pattern.
Figure 6:
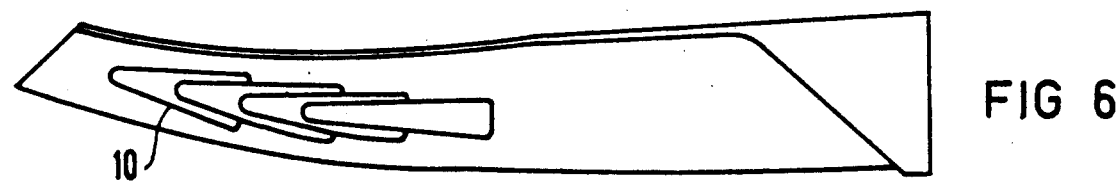
FIG. 6 is a side view of a portion of the handpiece of FIG. 1 illustrating a third modification of the line pattern.

In the embodiment or modification illustrated in FIG. 4, the longitudinally extending lines 5a coact with the transverse or cross extending lines 6a to form closed line patterns in the form of geometrical figures or patterns, such as the patterns 7 and 8. As shown in the left side of FIG. 4, the pattern 7 forms lozenges or patterns having a diamond shape or, if the sides and angles are equal of a rhombus-type pattern. The patterns 8 have a shape of elongated longitudinally extending rectangles. It is advantageous to arrange a plurality of the geometrical patterns, such as 7 and 8, in the gripping region, namely to provide them at the circumference of at least two quadrants that preferably lie diametrically opposite one another, as shown in FIG. 4. In FIGS. 5 and 6, the patterns 9, which have an enlarged rectangular shape, or pattern 10, which have a triangular shape overlap one another. It should be noted in the arrangement of these figures that the transversely proceeding lines, such as 6, are mainly present at the end of the gripping part adjacent the head housing 1, wherein the finger holds take particular effect.

Figure 7:
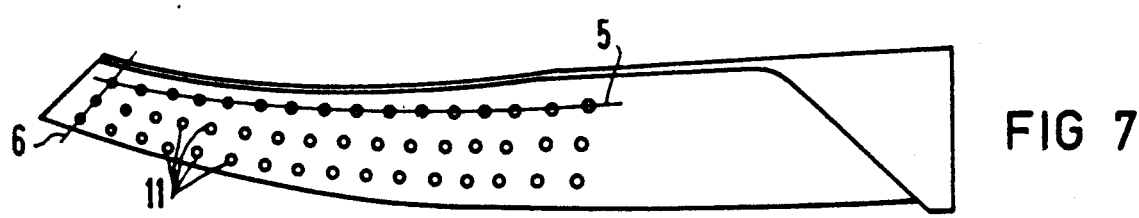
FIG. 7 is a side view of a portion of the handpiece of FIG. 1 illustrating a fourth modification of the line pattern.

The lines or, respectively, line patterns can also be interrupted, as shown in FIG. 7, and can be formed by roughened portions 11 that are joined to one another in a punctiform fashion. These portions 11 lie in lines or rows, such as lines 5 and 6, and extend both in the longitudinal direction of the handpiece and also across or transverse relative thereto. Even though it is possible to produce the lines or, respectively, the line patterns in a metallic grip part by sandblasting or etching, it is especially advantageous to produce these by roughening the surface with a laser beam. This has the particular advantageous that labeling of the handpiece can be undertaken with the same procedure.

It should be pointed out that the invention is not limited to the illustrated embodiments but that, on the contrary, it is conceivable and lies within the framework of the invention to also provide different shaped contours or, respectively, patterns on the grip part.

Although various minor modifications may be suggested by those versed in the art, it should be understood that we wish to embody within the scope of the patent granted hereon all such modifications as reasonably and properly come within the scope of our contribution to the art.

We claim:

1. In a dental handpiece having an elongated grip part provided with a surface that is a non-slip surface in comparison to the remaining surface of the handpiece, the improvements comprising the non-slip surface being formed by a plurality of thin lines having a roughened surface, said thin lines having first portions extending in a longitudinal direction of the handpiece, each of said lines having a second portion extending at an angle to the first portion to form a line pattern and said lines being arranged in at least two quadrants on the circumference of the grip part that lie diametrically opposite one another.

2. In a dental handpiece according to claim 1, wherein the lines are interrupted.

3. In a dental handpiece according to claim 1, wherein the line patterns form closed geometrical patterns.

4. In a dental handpiece according to claim 3, wherein a plurality of the geometrical patterns are arranged in close proximity.

5. In a dental handpiece according to claim 4, wherein the geometrical patterns are overlapping one another.

6. In a dental handpiece according to claim 1, wherein the lines are arranged on the surface of the handpiece part uniformly distributed over the circumference thereof.

7. In a dental handpiece according to claim 1, wherein the lines are produced by a partial roughening of the surface with a laser beam.

8. In a dental handpiece according to claim 1, wherein the lines are formed by partially sandblasting the surface of the handpiece.

9. In a dental handpiece according to claim 1, wherein the lines are formed by a partial etching of the surface of the handpiece.

10. In a dental handpiece according to claim 1, wherein the second portion of at least one line extends across a first portion of an adjacent line.

11. In a dental handpiece having a grip part provided with a surface that is a non-slip surface in comparison to the remaining surface of the handpiece, the improvement comprising the non-slip surface being formed by a plurality of thin lines having a roughened surface relative to a smooth surface of the remaining surface, said smooth surface being on each side of said thin lines and said thin lines having first portions extending in the longitudinal direction of the handpiece and second portions extending across the first portions to form line patterns and side lines being arranged in at least two quadrants on the circumference of the grip part that lie diametrically opposite one another.

12. In a dental handpiece according to claim 11, wherein the line patterns form closed geometrical patterns surrounding a portion of the smooth surface.

13. In a dental handpiece according to claim 12, wherein the geometrical patterns are overlapping one another.

14. In a dental handpiece according to claim 11, wherein said thin lines have a roughness free of edges and points which may damage rubber gloves worn by a person gripping the handpiece.

15. In a dental handpiece having a grip part provided with a surface that is a non-slip surface in comparison to the remaining surface of the handpiece, the improvements comprising the non-slip surface being formed by a plurality of punctiform portions having a roughened surface, said punctiform portions being arranged in rows extending in a longitudinal direction of the handpiece and being arranged in at least two quadrants on the circumference of the grip part that lie diametrically opposite one another.

* * * * *